United States Patent [19]
Smith et al.

[11] Patent Number: 5,645,561
[45] Date of Patent: Jul. 8, 1997

[54] UTERINE MANIPULATOR

[75] Inventors: Roger E. Smith, Bountiful; Eric M. King, West Jordan; David A. Bush, Bountiful, all of Utah

[73] Assignee: Utah Medical Products, Inc., Midvale, Utah

[21] Appl. No.: 283,382

[22] Filed: Jul. 29, 1994

[51] Int. Cl.$^6$ ............................................. A61M 29/00
[52] U.S. Cl. ..................................... 606/193; 604/55
[58] Field of Search ........................... 606/119, 193, 606/205, 208; 604/55

[56] References Cited

U.S. PATENT DOCUMENTS

| | | | |
|---|---|---|---|
| 2,482,622 | 9/1949 | Kahn | 128/348 |
| 3,809,091 | 5/1974 | Shute | 128/303 |
| 3,877,433 | 4/1975 | Librach | 128/303 |
| 4,000,743 | 1/1977 | Weaver | 128/303 |
| 4,022,208 | 5/1977 | Valtchev | 604/55 |
| 4,997,419 | 3/1991 | Lakatos et al. | 604/55 |
| 5,100,382 | 3/1992 | Valtchev | 604/96 |
| 5,104,377 | 4/1992 | Levine | 604/101 |
| 5,176,702 | 1/1993 | Boles et al. | 606/208 |
| 5,237,985 | 8/1993 | Hodgson et al. | 128/17 |
| 5,382,252 | 1/1995 | Failla et al. | 606/119 |
| 5,391,180 | 2/1995 | Tovey et al. | 606/205 |
| 5,409,496 | 4/1995 | Rowden et al. | 606/119 |
| 5,409,498 | 4/1995 | Braddock et al. | 606/139 |
| 5,487,377 | 1/1996 | Smith et al. | 600/204 |

*Primary Examiner*—Sam Rimell
*Assistant Examiner*—Pamela L. Wingood
*Attorney, Agent, or Firm*—Madson & Metcalf

[57] ABSTRACT

A hand-held gynecologic instrument for use in manipulating a uterus comprises an elongate body and a handle with a contour. An actuating lever used to control uterine movement is operable by the same hand that grips the handle. A uterus manipulation member pivotally connected to the elongate body comprises a tube formed with a shallow curve and fitted with an elastomeric tip and an irrigation conduit. The tube is releasably connected to a pivot block which has a tapered bore. A tapered bushing which mates with the bore is disposed about the tube. The tube and bushing are releasably secured by a nut to permit alteration of the effective length and rotational position of the tube to accommodate different uteruses. The pivot block is pivotally connected to the elongate body and to one end of a rod. The rod's other end is pivotally connected to the actuating lever to translate movement of the actuating lever into pivotal movement of the pivot block and hence into rotation of the tube about the anteverting axis. A membrane disposed about the tube is inflatable to exert resilient pressure for retaining the instrument in place without a tenaculum. A lever lock for locking the actuating lever comprises a biased member which has a prong for engaging teeth on the actuating lever. An adjacent cam member which includes a thumb-operable extension is used in moving the prong in and out of engagement with the teeth.

23 Claims, 4 Drawing Sheets

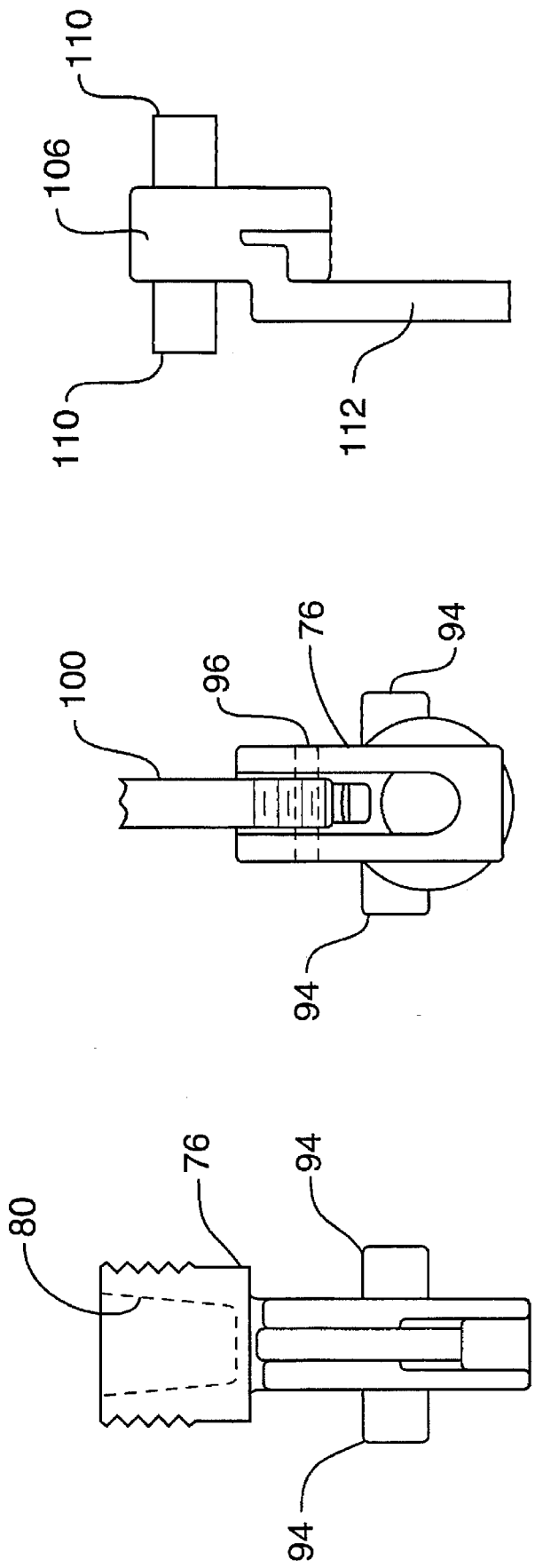

UTERINE MANIPULATOR

FIELD OF THE INVENTION

The present invention relates to a gynecological instrument for manipulating a uterus, and more particularly to a hand-held uterine manipulator having a uterus manipulation member that may be pivoted about either of two axes or locked in position by using a single hand.

TECHNICAL BACKGROUND OF THE INVENTION

In order to reduce the risks and recovery time associated with surgery, medical professionals have developed minimally invasive surgical procedures such as laparoscopy. During laparoscopy, a small incision is made in the patient's abdominal wall. Various surgical instruments are then partially inserted through the incision for use inside the abdominal cavity. For instance, laparoscopic procedures may be used in examining the female reproductive organs, in performing surgical procedures such as tumor removal and sterilization, and in collecting ova for in vitro fertilization.

However, the position of the patient's uterus may cause serious difficulties during such minimally invasive medical procedures. For instance, the uterus may obstruct the physician's view of the interior of the abdominal cavity, making it difficult or impossible to examine the uterus and other internal organs as needed. Moreover, the position of the uterus may interfere with surgical procedures by hindering the surgeon's access to the surgical site.

Various existing devices permit manipulation of the uterus during medical procedures. One uterine positioning device is denoted herein the "two-handed tenaculum manipulator," for reasons which will become apparent. The two-handed tenaculum manipulator includes a rigid bar and a rigid tube that are each pivotally connected at one end to a head. A rigid finger is also attached to the head, in the same plane as the bar and tube but at a right angle to them. The opposite ends of the bar and tube are pivotally connected to a spacer. The bar, tube, spacer, and head are thus connected in a parallelogram whose angles may be changed. By pivoting the spacer relative to the tube and the bar, one may pivot the head. Pivoting the head also moves the finger which is attached to the head. A locking screw is provided on the spacer for locking the spacer, tube, and bar into a selected position relative to one another.

In operation, the finger is inserted through the patient's vagina and cervix into the uterus, with the device's head pressing against the entrance to the cervix. A sharp wire hook with a handle, known collectively as a "tenaculum," is used to hook part of the cervix. The handle end of the tenaculum is then secured to a spring-loaded holder on the device's bar to maintain enough pressure on the device's head to keep the finger inside the uterus. A portion of the tube and bar are located inside the patient's vagina and cervix, while the spacer remains outside the patient.

Once the two-handed tenaculum manipulator is positioned in the uterus and secured by a tenaculum, movements of the spacer by the surgeon translate into movements of the finger, which in turn permit the surgeon to rotate the uterus about an anteverting axis and a cervical axis of rotation. The cervical axis is aligned with the patient's cervical passage. The anteverting axis is perpendicular to the cervical axis. By moving the spacer the surgeon may antevert the uterus, rotating it forward away from the spine. Conversely, the surgeon may retrovert the uterus, moving it back toward the spine. By locking the spacer in position and rotating the device about the longitudinal axis of the bar and tube, the surgeon may rotate the uterus to the left or right in an arc about the cervical axis.

The two-handed tenaculum manipulator may also be used to insert dyes, irrigation rinses, or other fluids into the uterus. A syringe or other source of fluid is attached to the external end of the tube. The finger is equipped with a conduit which communicates with the internal end of the tube, and with an opening at the tip of the finger.

In use, however, the two-handed tenaculum manipulator has several drawbacks. First, the use of a tenaculum to hold the device in place requires not merely puncturing the patient's internal tissue but also aggravating that injury by leaving the tenaculum hook in place and pulling on the hook. Even if the cervical tissue is "merely" clamped and pulled rather than being punctured, the resulting injury adds to the risks faced by the patient and often increases the patient's recovery period.

Another drawback of such a device is the lack of a convenient handle for holding and positioning the device. The two-handed tenaculum manipulator contains no grip which permits the surgeon to easily and reliably position the spacer relative to the tube and bar. At least two hands are needed to maintain control of the device's position, particularly if the device is covered with blood or other slippery fluids.

A further drawback, which becomes apparent once the spacer is positioned, is the need to use at least two hands to lock the finger in position about the anteverting axis. One hand is required to hold the spacer in the desired position relative to the tube while another hand tightens the locking screw. However, a surgeon often needs to hold at least two instruments at the same time. For example, the surgeon may need to hold a laparo-scope in place to ensure that the uterus remains in the desired position while the manipulator screw is tightened. Additional carefully coordinated assistance is then required because the surgeon cannot simultaneously lock the manipulator in position and hold the laparoscope in place.

An additional drawback of this device is its metal construction. Although exceptionally strong and rigid, the metal is electrically conductive and optically reflective. The device therefore has limited usefulness during electrosurgical or laser procedures.

Moreover, the two-handed tenaculum manipulator is expensive, so it must be reused. Before reuse, the device must be cleaned and sterilized. However, the complexity of the device makes it difficult and costly to clean.

A different uterine positioning device includes a curved rigid handle which contains a catheter. One end of the handle is inserted into the uterus until a stop on the handle abuts the vaginal side of the cervix. A balloon on the inserted end of the handle is then inflated against the uterine side of the cervix. Like the two-handed tenaculum manipulator, the curved handle device may be rotated to left or right to rotate the uterus about the cervical axis of rotation. One positive feature of such a curved handle device is its replacement of the tenaculum by the less traumatic stop and balloon combination.

A drawback of the curved handle device, however, is that it has no structure corresponding to the rotatable finger of the two-handed tenaculum manipulator. As a result, the degree to which the curved handle device may be used in anteverting or retroverting a uterus is extremely limited. When the curved handle device is initially inserted, one end of the device resides inside the uterus and another portion of the device is approximately centered within the patient's vaginal canal. Immediately after insertion, the angle of the uterus relative to the vaginal canal is therefore defined substantially by the degree of curvature of the device's handle. However, the handle curvature is fixed and the device lacks a rotatable finger. Thus, the uterus can be easily anteverted or retroverted away from this initial angle only by pressing the handle of the device against the vaginal canal. However, pressing the handle firmly against the vaginal tissue to alter the uterus' position may cause substantial injury to the vaginal tissue. The vaginal opening is particularly susceptible to rips or bruises caused in this manner. Moreover, the injury may be exacerbated if the pressure is sustained for any length of time while maintaining the uterus in the altered position.

Another drawback of the curved handle device is the lack of a convenient handle for holding and positioning the device. Like the two-handed tenaculum manipulator, the curved handle device contains no secure and comfortable grip which permits the surgeon to easily and reliably position the device. Positioning is particularly difficult along the curved longitudinal axis of the device.

Thus, it would be an advancement in the art to provide a uterine manipulator that is capable of maintaining its position relative to the uterus without hooking a tenaculum into the patient.

It would also be an advancement to provide a uterine manipulator that provides a reliable single-handed grip for positioning the manipulator to thereby position the uterus.

It would be a related advancement to provide a uterine manipulator capable of rotating the uterus about the cervical axis and also capable of rotating the uterus about the anteverting axis.

It would be a further advancement to provide a uterine manipulator which can be locked with one hand, thereby holding the uterus in a selected position about the anteverting axis.

It would be an additional advancement to provide such a uterine manipulator which is constructed almost entirely of nonconductive and nonreflective plastic.

It would also be an advancement to provide such a uterine manipulator which is designed and constructed so as to be a single use, disposable manipulator.

It would be a further advantage to provide such a uterine manipulator which is capable of introducing fluids into the uterus.

Such a uterine manipulator is disclosed and claimed herein.

BRIEF SUMMARY OF THE INVENTION

The present invention provides a hand-held gynecologic instrument for use by a surgeon in manipulating a uterus. In a presently preferred embodiment, the instrument comprises a rigid elongate body which has a proximate end and a distal end. The elongate body connects the external controls held by the surgeon to the internal structures used to manipulate the uterus. The elongate body is configured with rounded corners and a small outer diameter to ease insertion of the distal end into the patient's vagina.

The proximal end of the elongate body, which is retained outside the vaginal cavity during use, is connected to a handle. The handle has a pistol grip or similar contour which accommodates the grip of the surgeon's hand. The surgeon maintains a comfortable wrist angle while gripping the handle and manipulating the instrument because a portion of the handle is angularly disposed from the elongate body.

An actuating lever is used to control uterine movement about the anteverting axis. The actuating lever is pivotally connected to the instrument adjacent the handle. The actuating lever has two actuation surfaces configured to receive actuating pressures from at least one finger of the hand which is holding the instrument. The actuation surfaces are located opposite one another on the inside surface of a rigid loop that is large enough to accommodate one or more fingers. A surgeon using the instrument places within the loop at least one finger of the same hand that is gripping the handle. Thus, one hand is used both to hold the handle and to pivot the actuating lever forward or backward.

A manipulation member used to urge the uterus into various positions is pivotally connected to the distal end of the elongate body. A portion of the manipulation member is insertable into the patient's uterus to permit movement of the uterus in response to movement of the inserted portion. The manipulation member comprises an appendage having a tip end and a securement end. The appendage includes a stainless steel tube. The tip end includes an elastomeric tip for cushioning accidental impact of the appendage against the inside wall of the uterus. The tip end also comprises a curved portion which conforms more closely to the natural interior shape of the uterus than would a straight appendage.

The manipulation member further comprises an irrigation conduit for introducing a fluid such as a radio-opaque dye or an irrigation solution into the uterus. The irrigation conduit, which has an entry orifice and an exit orifice, is capable of receiving fluid from a fluid source at the entry orifice. The fluid is transported by pressure from the fluid source through the irrigation conduit and is discharged through the exit orifice into the interior of the patient's uterus.

The securement end of the appendage is releasably connected by an appendage securement to a pivot block which has an opening for receiving the securement end. The pivot block also has a tapered bore within an outer threaded portion. The appendage securement comprises a nut and a tapered bushing disposed about the appendage. The nut has an inner threaded portion for mating with the outer threaded portion of the pivot block. The tapered bushing mates with the tapered bore. Thus, the appendage is releasably secured to the pivot block by placing the securement end of the tube within the tapered bushing, placing the tapered bushing within the tapered bore, and threading the nut sufficiently onto the pivot block to press the tapered bushing against the tapered bore.

During use the appendage is typically secured in this manner by the appendage securement. However, the appendage may be released from engagement with the pivot block to adjust the effective length of the appendage, the rotational position of the curved portion of the appendage, or both. The effective length of the appendage is the length of that portion of the appendage which extends outside the appendage securement and the pivot block. The appendage's effective length may be altered to accommodate uteruses of varying sizes by loosening the nut, sliding the tube along its longitudinal axis relative to the tapered bushing, and tightening the nut. The curved tip portion of the appendage may be secured within the opening at a plurality of rotational orientations in order to accommodate variations in the positions and interior shapes of different uteruses. The appendage's rotational orientation may be changed by loosening the nut, rotating the tube about its longitudinal axis relative to the tapered bore, and tightening the nut.

The pivot block includes two spaced apart pivotal connection means. The pivot block is pivotally connected at a first point to the distal end of the elongate body. At a second point spaced apart from the first point, the pivot block is pivotally connected to one end of a rod. The other end of the rod is pivotally connected to the actuating lever. Thus connected, the rod translates pivotal movement of the actuating lever with respect to the elongate body into pivotal movement of the pivot block with respect to the elongate body, and hence into rotation of the appendage about the anteverting axis. The appendage is capable of rotating through a range of at least about ninety degrees.

By placing the appendage within the uterus and then moving the actuating lever, the surgeon urges a responsive movement of the uterus about the anteverting axis of rotation. In addition, by rotating the handle of the instrument about the longitudinal axis of the elongate body, the surgeon urges a responsive movement of the uterus about the cervical axis of rotation. Because one hand can simultaneously hold the instrument and urge such responsive movements of the uterus, the present invention permits surgeons to effectively manipulate the uterus with one hand, thereby leaving the other hand free to control another surgical instrument.

The preferred embodiment of the present invention also includes features which assist in maintaining the manipulated uterus in a desired position. An inflatable membrane is disposed about a portion of the tube and an inflation conduit is in fluid communication with a chamber inside the inflatable membrane. The inflation conduit is connectable to a fluid source and is capable of bidirectionally conveying a fluid to cause inflation and deflation of the inflatable membrane. A check valve is connected at one end of the inflation conduit to permit removal of the fluid source after inflation of the membrane. The check valve is manually releasable to permit deflation of the membrane for removal of the manipulator.

In operation, the appendage is placed within the uterus; the membrane is deflated during placement to permit easy passage of the appendage through the cervical canal. The membrane is then inflated to exert resilient pressure upon the uterine side of the cervix, while the nut presses against the vaginal side of the cervix. The combined pressure of the nut and the inflated membrane retain the instrument in place relative to the uterus, thereby making it unnecessary to secure the instrument by hooking the patient with a tenaculum. At the conclusion of the procedure, the membrane is deflated by manually releasing the check valve, thereby allowing withdrawal of the manipulator from within the uterus.

The instrument also includes a lever lock for locking the actuating lever in place. The lever lock, which is connected to the instrument adjacent the handle, is movable between a locked position and an unlocked position. When the lever lock is in the locked position it engages the actuating lever to prevent pivotal movement of the actuating lever relative to the elongate body. Fixing the actuating lever in place substantially fixes the angle of the appendage about the anteverting axis, and hence tends to fix the position of the uterus about that axis. When the lever lock is in the unlocked position it is disengaged from the actuating lever, thereby allowing pivotal movement of the actuating lever and hence permitting movement of the uterus about the anteverting axis. The lever lock is disposed and configured to permit a person to simultaneously and with one hand both hold the handle and move the lever lock between the locked position and the unlocked position.

To accomplish locking of the actuating lever, a portion of the actuating lever has a plurality of teeth and the lever lock comprises a biased member which has at least one prong for engaging the teeth. A cam member adjacent the biased member is capable of moving the prong relative to the teeth. The cam member includes an extension which extends from a cam-shaped portion of the cam member. The cam-shaped portion is pivotable by movement of the extension between a locked position and an unlocked position. The extension may be moved between the locked and unlocked positions by the thumb of the same hand that holds the instrument and operates the actuating lever.

When the cam-shaped portion is in the locked position the prong engages at least one of the teeth, thereby preventing pivotal movement of the actuating lever. By contrast, when the cam-shaped portion is in the unlocked position the prong is sufficiently free of the teeth to allow pivotal movement of the actuating lever and hence to allow rotation of the appendage about the anteverting axis. The prong is biased out of engagement with the teeth such that movement of the cam-shaped portion into the locked position overcomes the bias and urges the prong into engagement with the teeth.

These and other features and advantages of the present invention will become more fully apparent through the following description and appended claims taken in conjunction with the accompanying drawings.

BRIEF DESCRIPTION OF THE DRAWINGS

In order that the manner in which the above-recited and other advantages and features of the invention are obtained, a more particular description of the invention summarized above will be rendered by reference to the appended drawings. Understanding that these drawings only provide selected embodiments of the invention and are not therefore to be considered limiting of its scope, the invention will be described and explained with additional specificity and detail through the use of the accompanying drawings in which:

FIG. 4 is an end view of the pivot block with the tapered bore shown in phantom.

FIG. 5 is a bottom plan view illustrating the pivotal connection of the pivot block to the rod.

FIG. 7 is a top plan view of the biased member of the lever lock.

DETAILED DESCRIPTION OF THE PREFERRED EMBODIMENTS

Figure 1:
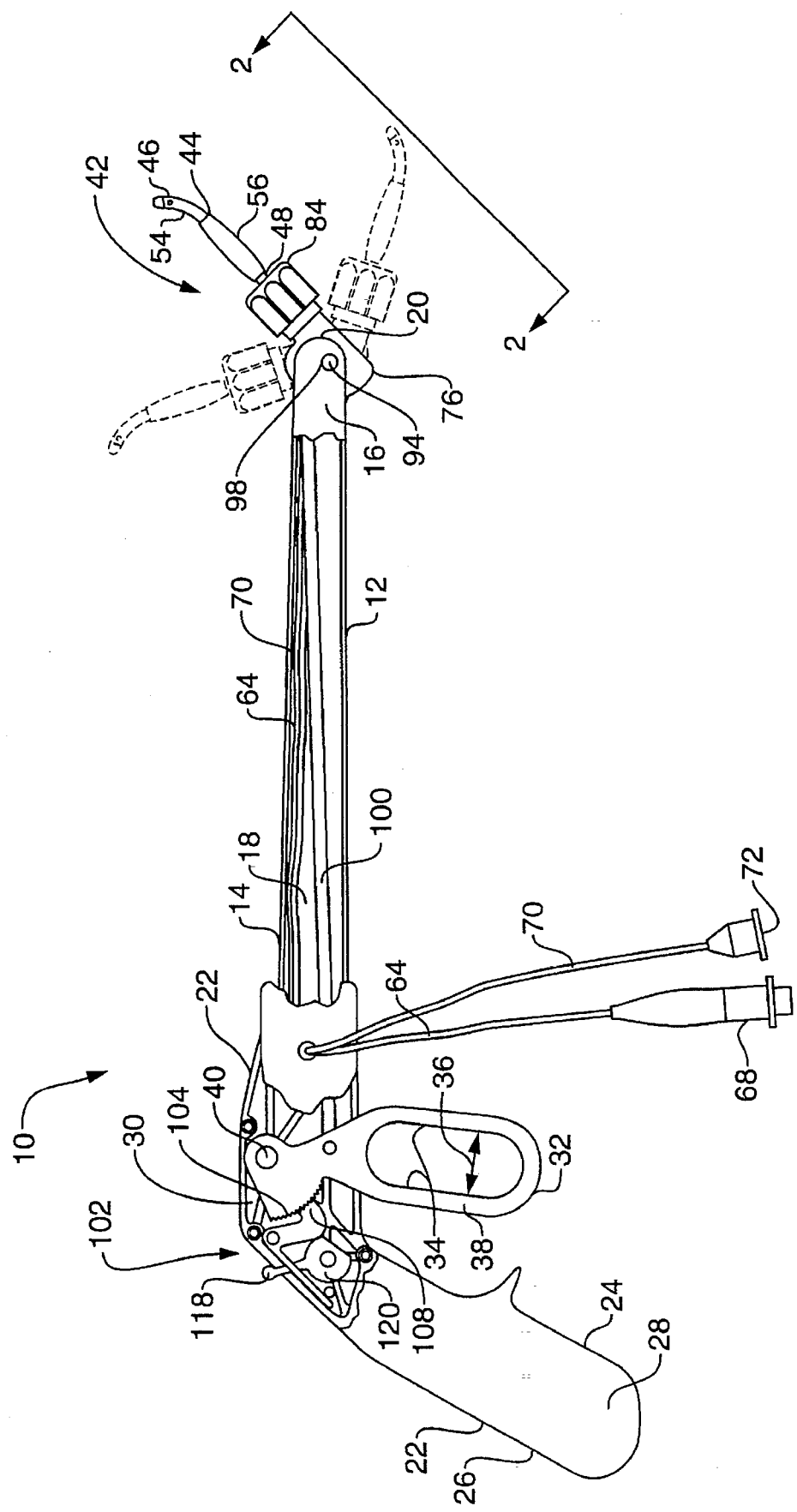
FIG. 1 is a partial cut away side view of a presently preferred embodiment of the instrument of the present invention, with alternate positions of the manipulation member shown in phantom.

Reference is now made to the figures wherein like parts are referred to by like numerals. The present invention relates to a hand-held gynecologic instrument for use by a surgeon in manipulating a patient's uterus. A presently preferred embodiment of the instrument is indicated generally at 10 in FIG. 1. The instrument 10 comprises a rigid elongate body 12 which connects external controls held by the surgeon to internal structures used to manipulate the uterus. The elongate body 12 has a proximate end 14 and a distal end 16. A longitudinal central cavity 18 is formed along substantially the entire length of the elongate body 12.

The elongate body 12 is configured to ease insertion of the distal end 16 within the patient's vaginal cavity. Thus, the elongate body 12 preferably has rounded corners 20 and a small outer diameter. The elongate body 12 is formed of metal, plastic, or another rigid material suitable for use in a sterile surgical environment. The presently preferred elongate body 12 is formed from a conventional high strength plastic or similar material by a standard injection molding process.

A handle 22 is connected to the proximate end 14 of the elongate body 12. The handle 22 has a contour 24 which accommodates the grip of the surgeon's hand. The presently preferred handle 22 includes a pistol grip contour 24. At least a portion 26 of the handle 22 is angularly disposed from the elongate body 12 rather than being substantially coaxial with the elongate body 12. Angular disposition of the contour 24 allows the surgeon to maintain a comfortable wrist angle while gripping the handle 22 and manipulating the instrument 10.

The presently preferred handle 22 includes a top piece 28 and a bottom piece 30 which mate to form the handle 22. The handle pieces 28 and 30 are formed of metal, plastic, or another rigid material suitable for use in a sterile surgical environment. The presently preferred handle pieces 28 and 30 are each formed separately from a conventional high strength plastic or similar material by a standard injection molding process. Next, additional components such as an actuating lever 32 and a lever lock 102 discussed below, are positioned against the handle pieces 28 and 30. Finally, the handle is completed by joining the top piece 28 to the bottom piece 30 with self-tapping screws or another conventional means.

The actuating lever 32, which is used to control uterine movement about the anteverting axis, is pivotally connected to the instrument 10 adjacent the handle 22. The actuating lever 32 has two actuation surfaces 34 which are configured to receive actuating pressures from at least one finger of the hand which is holding the instrument 10. The actuation surfaces 34 are located opposite one another across a gap 36 which is large enough to accommodate at least one finger. In the preferred embodiment illustrated in FIG. 1, the actuation surfaces 34 form part of the inside surface of a rigid loop 38. In an alternative embodiment, the actuation surfaces are positioned on opposite legs of a U-shaped portion of the actuating lever.

The actuating lever 32 is pivotally connected to the instrument 10 by cylindrical pivot bosses 40 which extend from the actuating lever 32 along a line normal to the viewing plane of FIG. 1. The pivot bosses 40 are rotatably secured within corresponding bearings (not shown) in the handle pieces 28 and 30. The bearings are cylindrical sleeves integral with the handle 22 which have an inside diameter slightly larger than the outside diameter of the pivot bosses 40. The actuating lever 32 is formed of a material such as the material used to form the handle 22 or the elongate body 12, and is formed by like processes.

A manipulation member used to urge the uterus into various positions is indicated generally at 42 in FIG. 1. The manipulation member 42 is pivotally connected to the distal end 16 of the elongate body 12. In the preferred embodiment shown, the manipulation member 42 comprises an appendage 44 having a tip end 46 and a securement end 48. As shown best in FIG. 2, the preferred appendage 44 comprises a tube 50, such as a stainless steel tube 50, which has an outer diameter of about 0.2 inches and which has a length of approximately 3.5 inches to permit adjustment of the protruding length 124 of the tube 50 in the range from about six centimeters to about eight centimeters.

Figure 8:
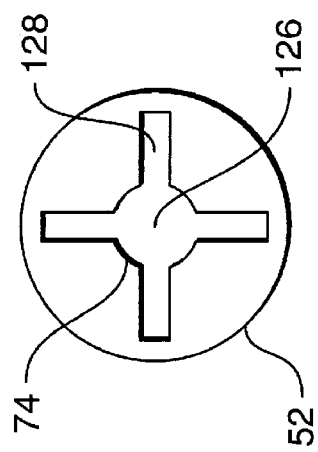
FIG. 8 is an end view of the elastomeric tip of the manipulation member shown in FIG. 2.

The tip end 46 of the appendage 44 preferably includes an elastomeric tip 52 which is formed of surgical rubber or a similar elastic material suitable for use in surgical instruments. The elastomeric tip 52 cushions impact of the tip end 46 against the interior wall of the uterus. The elastomeric tip 52 is secured to the tube 50 and to an irrigation conduit 70 by an adhesive or other conventional means. As shown in FIG. 8, the elastomeric tip 52 has an orifice 74 formed in the shape of a central hole 126 from which radiate a plurality of slots 128.

Figure 2:
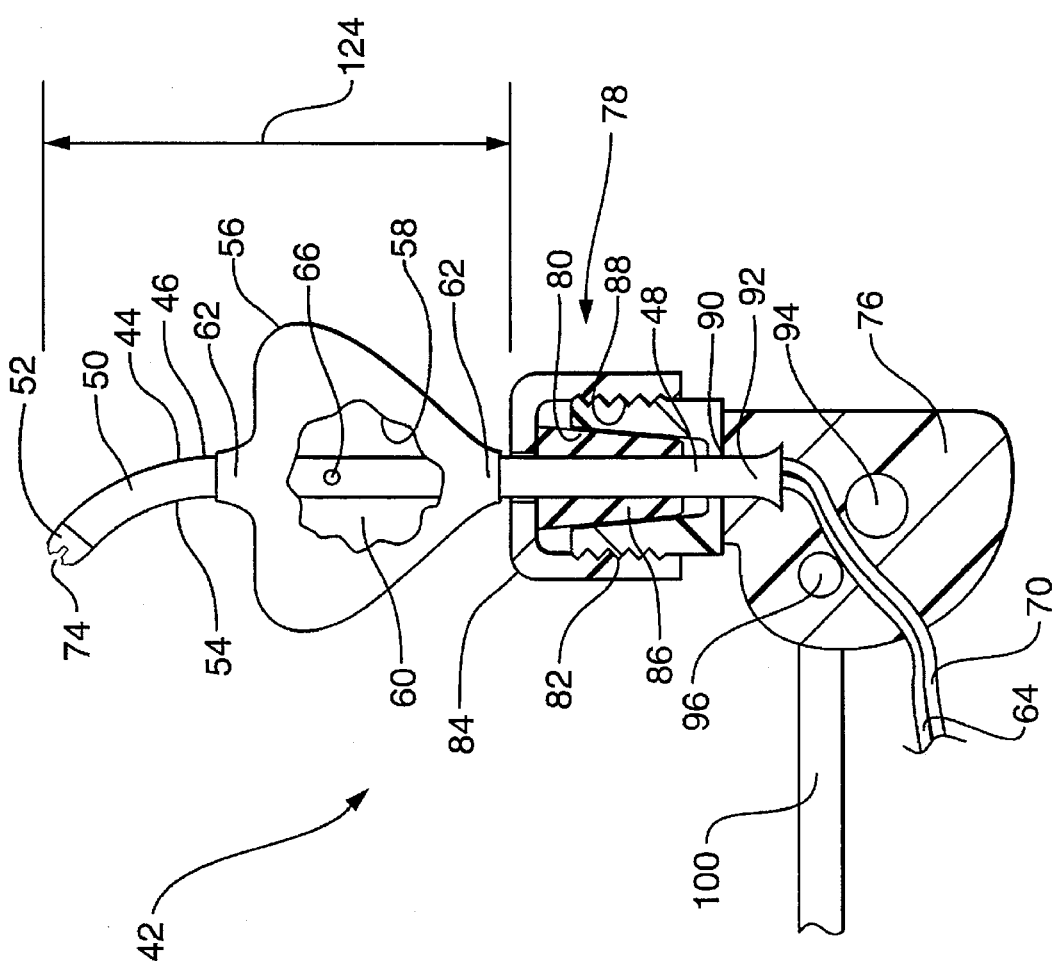
FIG. 2 is an enlarged view of the manipulation member of FIG. 1 shown in partial cross-section to illustrate the tapered bushing, the tapered bore, the nut, and the pivot block, with a portion of the inflated inflatable membrane cut away to illustrate the inflation conduit.

With reference to FIG. 2, the tip end 46 of the appendage 44 also preferably comprises a curved portion 54, such as the illustrated curved portion 54 which follows a shallow curve that facilitates insertion of the appendage 44 in the patient's uterus. The curved portion 54 allows the appendage 44 to conform more closely to the natural interior shape of the uterus than would a straight appendage 44. Although a particular shallow curve is illustrated, it will be appreciated that a variety of curves may be employed according to the teachings herein.

The presently preferred appendage 44 also comprises an inflatable membrane 56 which is used to secure the instrument 10 in place. The inflatable membrane 56, which is disposed about the tube 50, is movable between a deflated position illustrated in FIG. 1 and an inflated position shown in FIG. 2. In the deflated position an interior wall 58 (FIG. 2) of the inflatable membrane 56 is substantially adjacent the tube 50. In the inflated position, a portion of the inflatable membrane 56 is distended away from the tube 50 in response to the introduction of fluid into a chamber 60 between the interior wall 58 and the tube 50.

The chamber 60 is substantially defined by the tube 50 and the interior wall 58 of the inflatable membrane 56. The ends 62 of the membrane 56 are secured about the tube 50 by adhesive, circular clamps, or other conventional means to form a fluid-tight seal between the membrane 56 and the tube 50. The membrane 56 is formed of surgical rubber or any other suitable material.

Inflation and deflation are accomplished with an inflation conduit 64 which is in fluid communication with the chamber 60 via an orifice 66, as shown in FIG. 2. The presently preferred inflation conduit 64 comprises standard flexible plastic tubing of suitable diameter. With reference to FIG. 1, the inflation conduit 64 is connectable to a fluid source (not shown) at a connector 68. The presently preferred connector 68 includes a conventional manually releasable check valve which maintains pressure within the chamber 60 (FIG. 2) after the fluid source is disconnected from the inflation conduit 64. The fluid source may be a conventional syringe filled with a fluid such as a saline solution.

With reference to FIG. 1, the presently preferred instrument 10 also comprises the irrigation conduit 70, which has an entry orifice 72 and an exit orifice 74 (FIG. 2). The presently preferred irrigation conduit 70 comprises standard flexible plastic tubing of suitably small diameter. The irrigation conduit 70 is capable of receiving a fluid from a fluid source (not shown) at the entry orifice 72. The fluid is transported through the irrigation conduit 70 and discharged through the exit orifice 74 formed in the elastomeric tip 52 (FIG. 2) into the interior of the patient's uterus. During use the elastomeric tip 52 may be pressed tightly against tissue. The slotted design of the exit orifice 74, shown best in FIG. 8, results in a non-occludable fluid path. Thus, a fluid such as a radio-opaque dye or an irrigation solution may be introduced through the irrigation conduit into the uterus by the surgeon.

Figure 3:
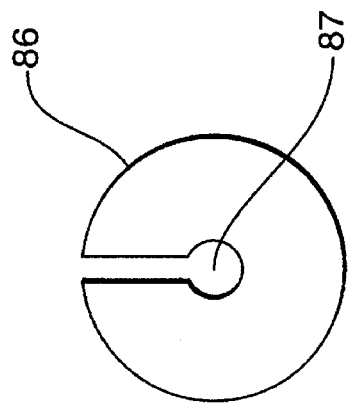
FIG. 3 is a top plan view of the tapered bushing.

With reference to FIG. 2, the securement end 48 of the appendage 44 is connected to a pivot block 76 by an appendage securement which is indicated generally at 78. The pivot block 76 has a tapered bore 80 within an outer threaded portion 82. The appendage securement 78 comprises a nut 84 and a tapered bushing 86. As illustrated in FIG. 3, the tapered bushing 86 is generally C-shaped in cross section, with a central cavity 87 for receiving the tube 50.

With reference to FIG. 2, the nut 84 has an inner threaded portion 88 for mating with the outer threaded portion 82 of the pivot block 76. The tapered bushing 86 mates with the tapered bore 80. The pivot block 76, the bushing 86, and the nut 84 are preferably formed of high strength plastic by conventional processes.

To releasably secure the appendage 44 to the pivot block 76 with the appendage securement 78, the securement end 48 of the appendage 44 is placed within the tapered bushing 86 and the tapered bushing 86 is placed within the tapered bore 80. Then the nut 84 is threaded onto the pivot block 76 sufficiently to press the tapered bushing 86 firmly against the tapered bore 80. Thus positioned, the securement end 48 of the tube 50 passes through an opening 90 in the pivot block. The tube 50 preferably comprises a fluted portion 92 which acts as a stop against the opening 90.

To accomplish pivotal movement about the anteverting axis, the pivot block 76 includes two spaced apart pivotal connection means 94 and 96. As shown in FIGS. 1 and 4, the pivot block 76 includes a pair of pivot bosses 94 for pivotally connecting the pivot block 76 to the distal end 16 of the elongate body 12. The pivot bosses 94 are rotatably secured in corresponding bearings 98 formed in the elongate body 12. Suitable bearings include orifices in the body 12 which have an inner diameter slightly larger than the outer diameter of the pivot bosses 94. Thus secured, the pivot block 76 is capable of rotating relative to the elongate body 12. The pivot block 76 is preferably capable of rotating through at least ninety degrees as indicated by the alternate positions shown in phantom in FIG. 1.

Control of the pivot block's movement about the anteverting axis is accomplished with the second connection means 96. As shown best in FIG. 5, the second connection means 96 provides a pivotal connection between the pivot block 76 and one end of a rod 100. The presently preferred connection means 96 is a pivot bushing 96 which is positioned for rotation within holes in the pivot block 76. The pivot bushing 96 contains a cross-drilled, tapped hole through which the threaded end of the rod 100 is screwed.

As shown in FIG. 1, the other end of the rod 100 is pivotally connected in a similar manner to the actuating lever 32. Thus connected, the rod 100 translates pivotal movement of the actuating lever 32 with respect to the elongate body 12 into pivotal movement of the pivot block 76 about the pivot bosses 94 and hence into rotation of the appendage 44 about the anteverting axis as shown in phantom. For clarity of illustration, FIG. 1 does not show in phantom the corresponding alternate positions of the actuating lever 32 and the rod 100, but those of skill in the art can readily determine these positions once the positions of the appendage 44 and the elongate body 12 are known.

Figure 6:
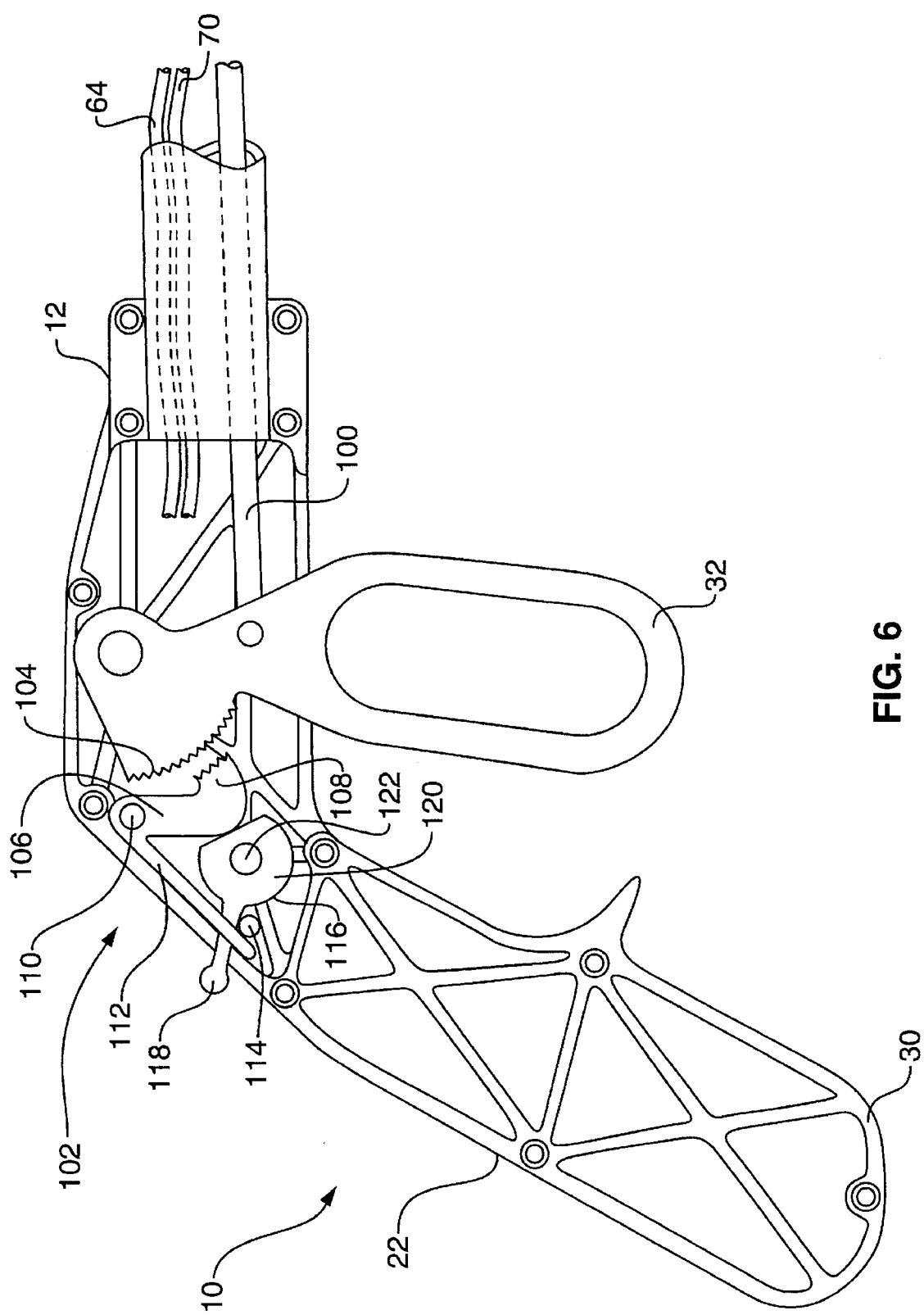
FIG. 6 is a partial cut away side view illustrating the actuating lever, the lever lock, and one side of the handle.

With reference to FIG. 6, the present invention also preferably includes a lever lock such as is indicated generally at 102. The lever lock 102 permits the surgeon to lock the appendage 44 (FIG. 1) in place at a selected angle of rotation about the anteverting axis. The lever lock 102 is movable between a locked position which prevents pivotal movement of the actuating lever 32 and an unlocked position which allows such pivotal movement of the actuating lever 32 and hence allows movement of the appendage 44 about the anteverting axis. Importantly, the lever lock 102 is disposed and configured to permit a surgeon to use the same hand to simultaneously hold the handle 22 and to operate the lever lock 102.

The actuating lever 32 includes a plurality of teeth 104, and the lever lock 102 comprises a biased member 106 which has at least one prong 108 for engaging the teeth 104. As further illustrated in FIG. 7, the biased member 106 has bosses 110 which engage corresponding bearings in the handle 22 to hold the biased member 106 in place. As shown in FIG. 6, the biased member 106 also has a spring arm 112 which is secured against a stop 114 that extends from the handle 22. The biased member 106 is formed of resilient high strength plastic or the like.

A cam member 116 adjacent the biased member 106 assists in moving the prong 108 in or out of engagement with the teeth 104. The cam member 116 includes an extension 118 which extends from a cam-shaped portion 120 of the cam member 116. The cam member 116 also has bosses 122 which rotatably secure the cam member 116 to the handle 22 via bearings in the handle 22. The cam member 116 is formed of high strength plastic or a similar material.

The cam-shaped portion 120 is pivotable by movement of the extension 118 between a locked position, shown in FIG. 1, and an unlocked position, shown in FIG. 6. Importantly, the extension 118 may be moved between the locked and unlocked positions by the thumb of the same hand that holds the handle 22.

In operation, the surgeon may adjust the appendage 44 shown in FIG. 2 before its insertion in uterus by changing the effective length 124 of the appendage 44, by altering the rotational position of the curved portion 54 with respect to the pivot block 76, or both. The effective length 124 of the appendage 44 is the length of that portion of the appendage 44 which extends outside the appendage securement 78 and the pivot block 76. The effective length 124 may be altered to accommodate uteruses of varying sizes by loosening the nut 84, sliding the tube 50 along the tube's longitudinal axis relative to the tapered bushing 86, and tightening the nut 84. The rotational orientation of the curved portion 54 may be changed to accommodate an anteverted uterus by loosening the nut 84, rotating the tube 50 about the tube's longitudinal axis relative to the tapered bore 80, and tightening the nut 84.

With reference to FIG. 1, the inflatable member 56 of the instrument 10 is deflated prior to insertion. The distal end 16 of the elongate body 12 is then inserted in the vaginal cavity until the nut 84 rests against the vaginal side of the cervix. In this position the appendage 44 is within the uterus. Insertion is eased by the rigidity, small outer diameter, and rounded corners 20 of the elongate body 12, and by the shallow curve 54 in the appendage 44.

After the appendage 44 is placed within the uterus, the inflatable membrane 56 is inflated by filling the chamber 60 with a fluid such as air or a saline solution. Thus inflated, the membrane 56 exerts resilient pressure upon the uterine side of the cervix, while the nut 84 presses against the vaginal side of the cervix. Although a flat headed nut 84 is illustrated, the nut 84 may also have a conical or tapered head to spread the pressure exerted by the nut 84 against the cervix. The combined pressure of the nut 84 and the inflated membrane 56 retain the instrument 10 in place relative to the uterus, thereby making it unnecessary to secure the instrument 10 by hooking the patient with a tenaculum.

As noted, the rod 100 translates movement of the actuating lever 32 into rotation of the appendage 44. Thus, by placing the appendage 44 within the uterus and then moving the actuating lever 32, the surgeon urges a responsive movement of the uterus about the anteverting axis of rotation. In addition, by rotating the handle 22 of the instrument 10 about the longitudinal axis of the elongate body 12, the surgeon urges a responsive movement of the uterus about the cervical axis of rotation. Importantly, the surgeon can simultaneously hold the instrument and urge such responsive movements of the uterus. The instrument 10 therefore permits surgeons to effectively manipulate the uterus with just one hand, leaving the other hand free to control another surgical instrument.

To accomplish such responsive movements, the surgeon grips the handle contour 24 shown in FIG. 1 with at least one finger and a portion of the palm of one hand. The surgeon also places at least one other finger of the same hand within the loop 32, and positions the thumb of that hand in proximity to the extension 118 of the lever lock 102. In this position, the surgeon can operate the instrument 10 with one hand and hence can manipulate the uterus with just one hand.

Importantly, the lever lock 102 can be operated with the same hand that holds the instrument 10, thereby permitting or preventing rotation of the appendage 44 about the anteverting axis. The extension 118 is placed and configured to allow the surgeon to move the extension 118 with the thumb of the hand that holds the instrument 10. Moving the extension 118 moves the cam-shaped portion 120 between the locked position shown in FIG. 1 wherein the prong 108 engages the teeth 104 and the unlocked position shown in FIG. 6 wherein the prong 108 is sufficiently free of the teeth 104 to allow movement of the actuating lever 32. The prong 108 is preferably biased out of engagement with the teeth 104 by the spring arm 112. Thus, movement of the cam-shaped portion 120 into the locked position overcomes the bias and urges the prong 108 into engagement with the teeth 104.

In summary, the present invention provides a uterine manipulator 10 that is capable of maintaining its position relative to the uterus by combined pressure from the inflatable membrane 56 and the nut 84 shown in FIG. 1. It is therefore unnecessary to hold the instrument 10 in position by hooking a tenaculum into the patient. Because the handle 22 and the actuating lever 32 are held and controlled by the same hand, the present invention also provides a reliable single-handed instrument capable of rotating the uterus about the cervical axis and the anteverting axis. The lever lock 102 can be locked with the same hand, thereby tending to fix the uterus in a selected position about the anteverting axis. Moreover, the irrigation conduit 70 provides the instrument 10 with the capability of introducing irrigation fluids and dyes into the uterus as appropriate.

The invention may be embodied in other specific forms without departing from its spirit or essential characteristics. The described embodiments are to be considered in all respects only as illustrative and not restrictive. Any explanations provided herein of the scientific principles employed in the present invention are illustrative only. The scope of the invention is, therefore, indicated by the appended claims rather than by the foregoing description. All changes which come within the meaning and range of equivalency of the claims are to be embraced within their scope.

What is claimed and desired to be secured by patent is:

1. A hand-held gynecologic instrument comprising:

a rigid elongate body having a proximate end and a distal end;

a manipulation member pivotally connected to said elongate body at said distal end;

a handle connected to said proximate end of said elongate body with at least a portion of said handle angularly disposed from said elongate body;

an actuating lever pivotally connected to said instrument adjacent said handle, said actuating lever disposed and configured to allow the same hand to simultaneously hold said handle and pivot said actuating lever; and a rod having a first end pivotally connected to said actuating lever and having a second end pivotally connected to said manipulation member such that said rod translates pivotal movement of said actuating lever with respect to said elongate body into pivotal movement of said manipulation member with respect to said elongate body, wherein said manipulation member comprises:

an appendage having a tip end and a securement end;

a pivot block having an opening for receiving said securement end of said appendage, said pivot block being pivotally connected to said rod and also pivotally connected to said elongate body at said distal end; and an appendage securement for securing in releasable engagement said securement end of said appendage within said opening of said pivot block, wherein said tip end of said appendage comprises a curved portion and wherein said appendage securement includes means for releasably securing said appendage within said opening of said pivot block at a plurality of rotational orientations and at various distances from said elongate body.

2. The gynecologic instrument of claim 1, wherein said handle has a contour to accommodate the grip of a hand.

3. The gynecologic instrument of claim 1, further comprising a lever lock connected to said instrument adjacent said handle, said lever lock movable between a locked position and an unlocked position, such that when in the locked position said lever lock engages said actuating lever to prevent pivotal movement of said actuating lever relative to said elongate body, and when in the unlocked position said lever lock is disengaged from said actuating lever allowing pivotal movement of said actuating lever, said lever lock being disposed and configured to permit a person using only one hand to simultaneously hold said handle and move said lever lock between said locked position and said unlocked position.

4. The gynecologic instrument of claim 1, wherein said manipulation member comprises an irrigation conduit having an entry orifice and an exit orifice, said irrigation conduit capable of receiving a fluid from a fluid source at said entry orifice for transport through said irrigation conduit and discharge through said exit orifice into the interior of a patient's uterus.

5. The gynecologic instrument of claim 1, further comprising:

an inflatable membrane disposed about at least a portion of said manipulation member; and an inflation conduit in fluid communication with said inflatable membrane, said inflation conduit connectable to a fluid source and capable of conveying a fluid to cause inflation and deflation of said inflatable membrane.

6. A hand-held gynecologic instrument comprising:

a rigid elongate body having a proximate end and a distal end;

a manipulation member pivotally connected to said elongate body at said distal end;

a handle connected to said proximate end of said elongate body and having a contour to accommodate the grip of a hand, at least a portion of said handle angularly disposed from said elongate body;

an actuating lever pivotally connected to said instrument adjacent said handle, said actuating lever having a first actuation surface and a second actuation surface for receiving actuating pressures from at least one finger of a hand which is holding said instrument, said first actuation surface located opposite from said second actuation surface across a gap large enough to accommodate the at least one finger, said actuating lever disposed and configured to allow the same hand to simultaneously hold said handle and to pivot said actuating lever by applying an actuating pressure to at least one of said actuation surfaces; and a rod having a first end pivotally connected to said actuating lever and having a second end pivotally connected to said manipulation member such that said rod translates pivotal movement of said actuating lever with respect to said elongate body into pivotal movement of said manipulation member with respect to said elongate body; and a lever lock connected to said instrument adjacent said handle, said lever lock movable between a locked position and an unlocked position, such that when in the locked position said lever lock engages said actuating lever to prevent pivotal movement of said actuating lever relative to said elongate body, and when in the unlocked position said lever lock is disengaged from said actuating lever allowing pivotal movement of said actuating lever, said lever lock being disposed and configured to permit a person using only one hand to simultaneously hold said handle and move said lever lock between said locked position and said unlocked position, wherein said manipulation member comprises:

an appendage having a tip end and a securement end;

a pivot block having an opening for receiving said securement end of said appendage, said pivot block being pivotally connected to said rod and also pivotally connected to said elongate body at said distal end; and an appendage securement for securing in releasable engagement said securement end of said appendage within said opening of said pivot block, wherein said pivot block has a tapered bore within an outer threaded portion, said appendage securement comprises a nut having an inner threaded portion for mating with said outer threaded portion of said pivot block, and said appendage securement further comprises a tapered bushing disposed about said appendage for mating placement within said tapered bore, whereby said appendage may be locked at various rotational orientations and said tip end of said appendage may be locked at various distances from said elongate body, by threading said nut sufficiently onto said pivot block to secure said tapered bushing against said tapered bore and about said appendage.

7. The gynecologic instrument of claim 6, wherein said tip end of said appendage comprises an elastomeric tip for cushioning impact of said appendage against a patient's uterus.

8. The gynecologic instrument of claim 6, wherein said pivot block is pivotally connected to said elongate body and to said rod such that pivotal motion of said pivot block moves said appendage in a plane substantially parallel to said angularly disposed portion of said handle.

9. The gynecologic instrument of claim 6, wherein said pivot block is pivotally connected to said elongate body and to said rod such that pivotal motion of said pivot block is capable of moving said appendage through a range of at least about ninety degrees about an axis that is substantially transverse to said elongate body.

10. The gynecologic instrument of claim 6, wherein said first actuation surface and said second actuation surface of said actuating lever form part of a loop through which a user may place at least one finger of the hand which is holding said instrument.

11. The gynecologic instrument of claim 6, wherein said manipulation member comprises an irrigation conduit having an entry orifice and an exit orifice, said irrigation conduit capable of receiving a fluid from a fluid source at said entry orifice for transport through said irrigation conduit and discharge through said exit orifice into the interior of a patient's uterus.

12. The gynecologic instrument of claim 6, further comprising:

an inflatable membrane disposed about at least a portion of said manipulation member; and an inflation conduit in fluid communication with said inflatable membrane, said inflation conduit connectable to a fluid source and capable of conveying a fluid to cause inflation and deflation of said inflatable membrane.

13. The gynecologic instrument of claim 12, wherein one end of said inflation conduit comprises a check valve.

14. The gynecologic instrument of claim 6, wherein a portion of said actuating lever has a plurality of teeth, and wherein said lever lock comprises:

a biased member having at least one prong for engaging said teeth of said actuating lever; and a cam member adjacent said biased member and capable of moving said at least one prong with respect to said teeth, said cam member having an extension extending from a cam-shaped portion, said cam-shaped portion pivotable by movement of said extension between a locked position and an unlocked position, such that when in said locked position said prong engages at least one of said teeth to prevent pivotal movement of said actuating lever, and when in said unlocked position said prong is sufficiently free of said teeth to allow pivotal movement of said actuating lever.

15. The gynecologic instrument of claim 14, wherein said biased member further comprises a biasing means for urging said prong out of engagement with said teeth, and said lever lock is further characterized in that when said cam member is in said locked position said cam-shaped portion overcomes said biasing means by urging said prong into engagement with at least one of said teeth to prevent pivotal movement of said actuating lever.

16. A hand-held gynecologic instrument comprising:

a rigid elongate body having a proximate end and a distal end;

a manipulation member pivotally connected to said elongate body at said distal end;

a handle connected to said proximate end of said elongate body and having a contour to accommodate the grip of a hand, at least a portion of said handle angularly disposed from said elongate body;

an actuating lever pivotally connected to said instrument adjacent said handle, said actuating lever having a plurality of teeth, said actuating lever comprising a loop having a first actuation surface and a second actuation surface located opposite one another across a gap large enough to accommodate at least one finger, said loop disposed and configured to allow the same hand to simultaneously hold said handle and to pivot said actuating lever by applying an actuating pressure to at least one of said actuation surfaces; and a rod having a first end pivotally connected to said actuating lever and having a second end pivotally connected to said manipulation member such that said rod translates pivotal movement of said actuating lever with respect to said elongate body into pivotal movement of said manipulation member with respect to said elongate body; and a lever lock connected to said instrument adjacent said handle, said lever lock movable between a locked position and an unlocked position, such that when in the locked position said lever lock engages said actuating lever to prevent pivotal movement of said actuating lever relative to said elongate body, and when in the unlocked position said lever lock is disengaged from said actuating lever allowing pivotal movement of said actuating lever, said lever lock being disposed and configured to permit a person using only one hand to simultaneously hold said handle and move said lever lock between said locked position and said unlocked position, said lever lock comprising:

a biased member having at least one prong for engaging said teeth of said actuating lever; and a cam member adjacent said biased member and capable of moving said at least one prong with respect to said teeth, said cam member having an extension extending from a cam-shaped portion, said cam-shaped portion pivotable by movement of said extension between a locked position and an unlocked position, such that when in said locked position said prong engages at least one of said teeth to prevent pivotal movement of said actuating lever, and when in said unlocked position said prong is sufficiently free of said teeth to allow pivotal movement of said actuating lever wherein said manipulation member comprises:

an appendage having a tip end and a securement end;

a pivot block having an opening for receiving said securement end of said appendage, said pivot block being pivotally connected to said rod and also pivotally connected to said elongate body at said distal end; and an appendage securement for securing in releasable engagement said securement end of said appendage within said opening of said pivot block, wherein said appendage securement includes means for releasably securing said appendage within said opening of said pivot block at a plurality of rotational orientations and at various distances from said elongate body.

17. The gynecologic instrument of claim 16, wherein said tip end of said appendage comprises an elastomeric tip for cushioning impact of said appendage against a patient's uterus.

18. The gynecologic instrument of claim 16, wherein said pivot block is pivotally connected to said elongate body and to said rod such that pivotal motion of said pivot block moves said appendage in a plane substantially parallel to said angularly disposed portion of said handle.

19. The gynecologic instrument of claim 16, wherein said pivot block is pivotally connected to said elongate body and to said rod such that pivotal motion of said pivot block is capable of moving said appendage through a range of at least about ninety degrees about an axis that is substantially transverse to said elongate body.

20. The gynecologic instrument of claim 16, wherein said pivot block has a tapered bore within an outer threaded portion, said appendage securement comprises a nut having an inner threaded portion for mating with said outer threaded portion of said pivot block, and said appendage securement further comprises a tapered bushing disposed about said appendage for mating placement within said tapered bore, whereby said appendage may be locked at various rotational orientations and said tip end of said appendage may be locked at various distances from said elongate body, by threading said nut sufficiently onto said pivot block to secure said tapered bushing against said tapered bore and about said appendage.

21. The gynecologic instrument of claim 16, wherein said manipulation member comprises an irrigation conduit having an entry orifice and an exit orifice, said irrigation conduit capable of receiving a fluid from a fluid source at said entry orifice for transport through said irrigation conduit and discharge through said exit orifice into the interior of a patient's uterus.

22. The gynecologic instrument of claim 16, further comprising:

an inflatable membrane disposed about at least portion of said manipulation member; and an inflation conduit in fluid communication with said inflatable membrane, said inflation conduit connectable to a fluid source and capable of conveying a fluid to cause inflation and deflation of said inflatable membrane.

23. The gynecologic instrument of claim 22, wherein one end of said inflation conduit comprises a check valve.

* * * * *